United States Patent
Kumar et al.

(10) Patent No.: US 6,916,935 B2
(45) Date of Patent: Jul. 12, 2005

(54) LOSARTAN POTASSIUM SYNTHESIS

(75) Inventors: Ashok Kumar, Mumbai (IN);
Rajeshkumar Singh, Mumbai (IN);
Nalinakshya Panda, Vasai West (IN);
Abhay Upare, Mumbai (IN);
Manmohan Nimbalkar, Mumbai (IN);
Satish Soudagar, Mumbai (IN)

(73) Assignee: Ipca Laboratories, Mumbai (IN)

( * ) Notice: Subject to any disclaimer, the term of this patent is extended or adjusted under 35 U.S.C. 154(b) by 11 days.

(21) Appl. No.: 10/431,847

(22) Filed: May 7, 2003

(65) Prior Publication Data

US 2004/0224998 A1 Nov. 11, 2004

Related U.S. Application Data

(60) Provisional application No. 60/468,208, filed on May 6, 2003.

(51) Int. Cl.[7] .............................................. C07D 257/00

(52) U.S. Cl. ...................................................... 548/252
(58) Field of Search ........................... 548/252; 514/381

(56) References Cited

U.S. PATENT DOCUMENTS 6,710,183 B2 * 3/2004 Fischer et al. .............. 548/252

OTHER PUBLICATIONS

Louise M.Burrell, Drug Safety, 1997, 16(1), pp. 56–65.*
Louise M.Burrell, 1997, 16(1), CAS: 126: 152290.*

* cited by examiner

*Primary Examiner*—Rita Desai
*Assistant Examiner*—Robert Shiao
(74) *Attorney, Agent, or Firm*—Pharmaceutical Patent Attorneys, LLC

(57) ABSTRACT

A process for the synthesis of Losartan Potassium by reacting Trityl Losartan in a primary alcohol with potassium tertiary alkoxide.

7 Claims, No Drawings

LOSARTAN POTASSIUM SYNTHESIS

RELATED APPLICATIONS

This application claims priority from U.S. provisional patent application Ser. No. 60/468,208, filed 6 May 2003, and further claims priority from India National patent application Serial No. 335/MUM/2003, filed 3 Apr. 2003.

GOVERNMENT INTEREST

None.

TECHNICAL FIELD

The invention is related to an improved process for the synthesis of Losartan Potassium, an angiotensin II receptor antagonist.

BACKGROUND

Among cardiovascular drugs, Angiotensin II receptor antagonists like losartan potassium are prominently used as an active ingredient in the management of hypertension. Losartan potassium plays an effective role in patients having difficulty in tolerating ACE inhibitors. The chemical name of losartan potassium is 2-n-Butyl-4-Chloro-1[((2'-tetrazol-5-yl)-1,1'-bisphenyl-4-yl)methyl]-imidazole-5-methanol potassium.

It is known in the art to synthesize losartan potassium from the acid form of losartan. Losartan potassium (shown as the compound of formula (I) below) is known in the art as able to be synthesized by reacting its acid (shown as the compound of formula (II) below) with KOH. The intermediate acid form (II) in turn is known as able to be synthesized by detritylation of 2-n-butyl-4-chloro-5-hydroxymethyl-1-[((2'-triphenylmethyltetrazole-5-yl)biphenyl-4-yl)methyl] imidazole (shown as the compound of formula (III) below).

The synthesis of Trityl Losartan (the reactant of form (I) below) is known in the art. See 34 J. MED. CHEM. 2525–27 (1991); 59 J. ORG. CHEM. 6391–94 (1994) U.S. Pat. No. 5,138,069). Trityl Losartan (and the Losartan acid) and may alternatively be prepared using the reactions and techniques described in U.S. Pat. No. 5,138,069 and patent application number WO93/10106.

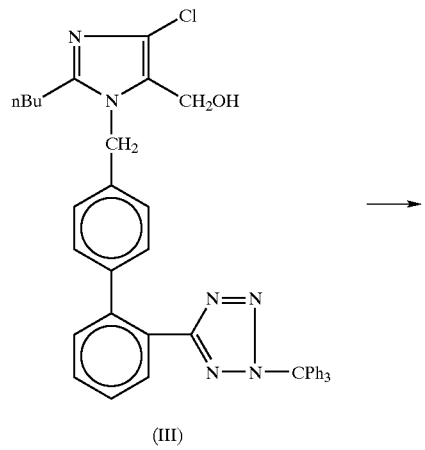

(III)

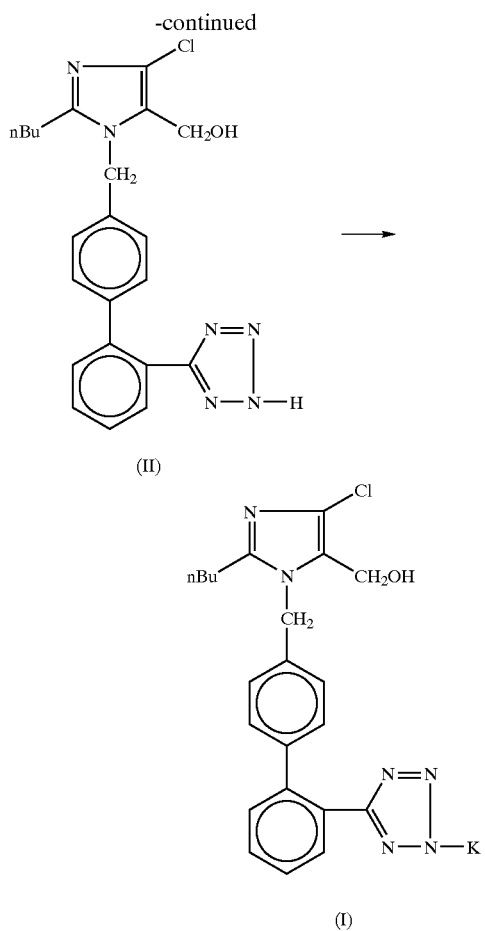

The preparation from Trityl Losartan (the reactant of form (III)) of Losartan acid (II) by acid-catalyzed cleavage of the trityl group from Trityl Losartan (III) is disclosed in U.S. Pat. No. 5,281,603. Another method disclosed to prepare Losartan acid from trityl losartan is disclosed in U.S. Pat. No. 5,281,604; in this process, Trityl Losartan (III) is refluxed in a mixture of methanol and tetrahydrofuran for 18 hours to get losartan acid (II).

Similarly, in patent application number WO01/81336, Richter Gedeon describes treatment of Trityl Losartan (III) with potassium hydroxide in primary alcohols and crystallization of the product (I) from methanol with the help of anti-solvents such as dipolar aprotic solvent (acetonitrile), aprotic solvent (straight or branched chain or cyclic aliphatic hydrocarbons) or a protic solvent (sec-butanol).

The Richter Gedeon approach was found to be easy and superior to the existing methods, however was found to suffer from various drawbacks as summarized below:
a) The product obtained does not pass desired solubility in various solvents. To make the product improve in quality, it needs an extra purification as per the Richter Gedeon application.
b) Purification step in the process, the resultant purity and the yields thereof, depend on very precise ratios of solvent mixture (e.g. methanol, cyclohexane or acetonitrile)
c) High volume of solvents in combination is used in purification which leads to capacity reduction of plant production/facilities.
d) Recovery and recyclability of the solvents (methanol and anti-solvents) from its mixture is difficult and needs careful purification by distillation to get recyclable solvents. Production of waste is more with no economic value and high pollution load in the non-recovery option.

Patent application number WO 02/094816, discloses use of acetone, ethyl acetate, acetonitrile and toluene as anti-solvents and has similar problems of recovery and reuse of solvents and high cost of production. Since isolation of the product is simply by precipitation using anti-solvents, the product needs further purification to pass the required tests, in this case also.

The art teaches not only the need for purifying the resulting losartan potassium (I), the art teaches various methods to purify it. For example, U.S. Pat. No. 5,608,075 discloses two polymorphic forms of Losartan Potassium, which are form I and form II. Their method of preparation and characterization by X-ray powder diffraction pattern, DSC thermograms, FT-IR spectra, Raman spectra and $C^{13}$ NMR (solid state) spectra is also given. The disclosed procedure for polymorphic form I is the addition of aqueous solution of (I) to a refluxing mixture of cyclohexane and isopropyl alcohol followed by azeotropic distilling out cyclohexane/isopropyl alcohol/water ternary azeotrope at 64° C. while the form I crystallizes out at 69° C.

Patent application number WO 98/18787 describes a method which also starts with a solution of Losartan Potassium (I) in aqueous isopropyl alcohol and is heated to distill out water-isopropyl alcohol mixture to lower the water content to 2.6%. Further excessive seeding is carried out with slurry of Losartan Potassium (I) in cyclohexane until the seed remains undissolved. The precipitation of the product is then achieved by continuous distillation of ternary azeotrope with simultaneous addition of cyclohexane to the reaction mass. This azeotrope distillation is carried out until moisture level decreases to about 0.2 to 0.11%. The crystallized product thus obtained is filtered.

SUMMARY OF INVENTION

The invention is related to a process for the synthesis of Losartan Potassium of formula (I), which comprises detritylation of Trityl Losartan of formula (III) in a primary alcohol (we use the term "primary alcohol" to mean an alcohol of the structure R—OH, wherein the R group is a C1 to approximately C4 chain) with a potassium tertiary alkoxide (e.g., potassium tertiary butoxide) as a reagent, without needing to isolate the corresponding free acid of formula II. The Losartan Potassium product is isolated by crystallization from a solvent such as Isopropyl alcohol or tetrahydrofuran, or, optionally, a combination of both in a suitable ratio.

DETAILED DESCRIPTION

The invention deals with the single pot synthesis of Losartan Potassium (I) of very high purity. The process starts with Trityl Losartan (III), but uses a single solvent such as isopropyl alcohol or tetrahydrofuran. This leads to reduction of the solvent usage and losses. This process eliminates the need for extra purification of (I). The use of single solvents (isopropyl alcohol or tetrahydrofuran) also makes the single solvent easily recoverable and reusable in the process, reducing the cost of production significantly.

In an optional embodiment a combination of isopropyl alcohol and tetrahydrofuran in suitable proportions have also been used, giving high yields and purity. However, in this case the solvent mixture require fractional distillation after recovery.

The present process involves refluxing a mixture of Trityl Losartan (III) and an equimolar amount of potassium tertiary butoxide (KOBut) together in solvent comprised of a primary alcohol. The primary alcohol is preferably present in a volume of from three to six times the volume with respect to the Trityl Losartan (II). We prefer the reaction be maintained for about 3–10 hours, preferably for 4–8 hours, albeit reaction times may be adjusted depending on solvent concentration, temperature, etc. . . . Regardless of the specific reaction conditions used, one can monitor the reaction progress by Thin Layer Chromatography, to assess completion.

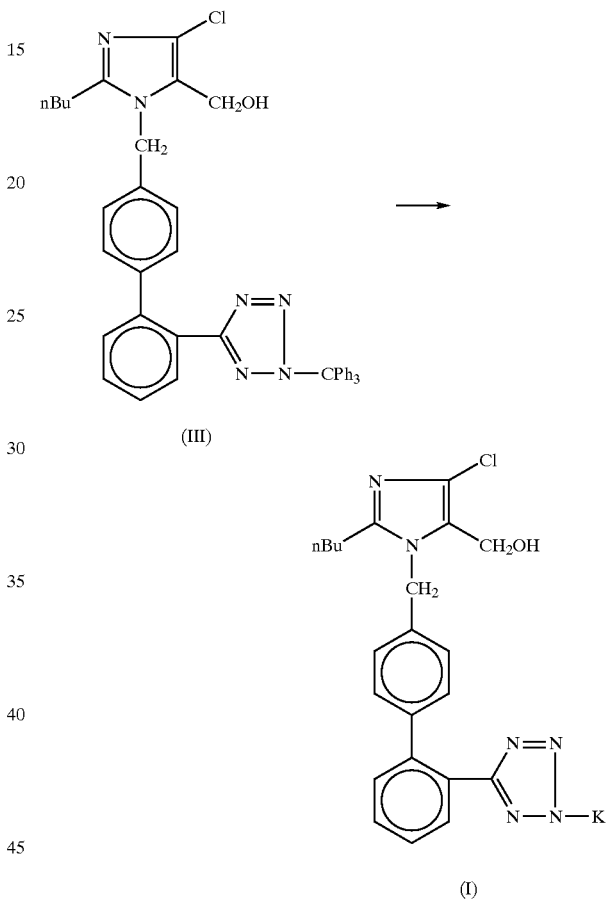

After detritylation, the reaction mixture is cooled down to 0 to −10° C. This cooling may be done with the primary alcohol present, or after it is substantially removed. We prefer that it is done after about 50% of the primary alcohol is removed. The product is then filtered to remove the by-product (namely trityl methyl ether). The filtered reaction mass is then concentrated to remove primary alcohol. It is preferable to remove primary alcohol before crystallizing the product from isopropyl alcohol or tetrahydrofuran, but the complete removal up to the last traces is not essential, as far as quality of the product is concerned.

The advantage of the modified process disclosed herein over prior art is that the product contains almost similar chemical profile, but the new process gives a product of high quality which meets current drug substance purity requirements, without requiring extra purification step. Another major advantage of this process is the use of a single solvent (isopropyl alcohol or tetrahydrofuran), which requires only 1.0–6.0 times the volume of solvent, as compared to larger volumes of solvents (as is done in prior art solvent mixtures). Similarly, the use of a single solvent improves solvent recovery and reusability, making the process cost effective, eco-friendly as well as plant friendly.

The following examples of the present invention are illustrated:

EXAMPLE 1

Under nitrogen atmosphere in a 500 ml flask, a solution of potassium tertiary butoxide (8.44 gm, 0.075 mole) in methanol (275 ml) is prepared. To this solution, 50.0 gm of trityl losartan (0.075 mole) is added. The mixture is refluxed for 8 hours. The completion of reaction is monitored on TLC. After satisfactory completion, the reaction mass is concentrated to 50%, and cooled to approximately −5° C. The reaction mass is filtered to separate the reaction product from the reaction by-product. After charcoalisation of the filtrate, it is filtered through celite. Residual methanol is then distilled out substantially completely and stripped out using isopropyl alcohol (25 ml each) twice. Isopropyl alcohol (75 ml) is charged and kept for 12 hours at 25–30° C. The reaction mass is then cooled to 0–5° C. and filtered. The resulting product, Losartan Potassium, is then washed with chilled isopropyl alcohol (15 ml). The final product is dried at 45–50° C. under vacuum for 6 hours to remove residual isopropyl alcohol. The percentage yield of Losartan Potassium is 81.63%.

EXAMPLE 2

Under nitrogen atmosphere in a 500 ml flask, a solution of potassium tertiary butoxide (8.44 gm, 0.075 mole) in methanol (275 ml) is prepared. To this solution, 50.0 gm of trityl losartan (0.075 mole) is added and refluxed for 8 hours. The completion of reaction is monitored on TLC. The reaction mass is concentrated to 50% and cooled to −5±2° C. The by-product is removed by filtration. After charcoalisation, the filtrate is filtered through celite. Methanol is distilled out until a sticky mass is obtained. Isopropyl alcohol (75 ml) is charged and cooled to 30° C. This reaction mass is kept for 12 hours and then it is cooled to 0–5° C. The product (Losartan Potassium) is filtered and washed with chilled isopropyl alcohol (15 ml). The final product is dried at 45–50° C. under vacuum for 6 hours to remove residual isopropyl alcohol. The percentage yield of Losartan Potassium is 78%.

EXAMPLE 3

Under nitrogen atmosphere in a 500 ml flask, a solution of potassium tertiary butoxide (8.44 gm, 0.075 mole) in methanol (275 ml) is prepared. To this solution, 50.0 gm trityl losartan (0.075 mole) is added and refluxed for 8 hours. The completion of reaction is monitored on TLC. The reaction mass is concentrated to 50% and cooled to −5±2° C. The by-product is removed by filtration. After charcoalisation, the filtrate is filtered through celite. Methanol is distilled out. Terahydrofuran (200 ml) is charged and refluxed for 1.0 hour. The reaction mass is cooled to 30° C. and stirred for 5 hours. The reaction mass is cooled to 0–5° C. and filtered. The product (Losartan Potassium) is washed with chilled tetrahydrofuran (15 ml). The final product is dried at 45–50° C. under vacuum for 6 hours. The percentage yield of Losartan Potassium is 90.62%.

EXAMPLE 4

Under nitrogen atmosphere in a 500 ml flask, a solution of potassium tertiary butoxide (8.44 gm, 0.075 mole) in methanol (275 ml) is prepared. To this solution, 50.0 gm trityl losartan (0.075 mole) is added and refluxed for 8 hours. The completion of reaction is monitored on TLC. The reaction mass is cooled to −5±2° C. and the by-product obtained is filtered away. After charcoalisation, the filtrate is filtered through celite. Methanol is distilled out completely and stripped out using 25 ml of isopropyl alcohol. Isopropyl alcohol (75 ml) is charged and kept for 12 hour. The reaction mass is cooled to 0–5° C. and filtered. The product (Losartan Potassium) is washed with chilled isopropyl alcohol (15 ml). The final product is dried at 45–50° C. under vacuum for 6 hours. The percentage yield of Losartan Potassium is 79.95%.

EXAMPLE 5

Under nitrogen atmosphere in a 500 ml flask, a solution of potassium tertiary butoxide (8.44 gm, 0.075 mole) in methanol (275 ml) is prepared. To this solution, 50.0 gm trityl losartan (0.075 mole) is added and refluxed for 8 hours. The completion of reaction is monitored on TLC. The reaction mass is concentrated to 50% and cooled to −5±2° C. The by-product is removed by filtration. After charcoalisation, the filtrate is filtered through celite. The remaining methanol is then distilled out. Tetrahydrofuran (120 ml) is charged and the reaction mass stirred at 50–55° C. for 15 minutes. The reaction mass is cooled to 30° C. and stirred for 5 hours. The reaction mass is then cooled to 0–5° C. and filtered. The product (losartan potassium) is washed with chilled tetrahydrofuran (15 ml). The final product is dried at 45–50° C. under vacuum for 6 hours, to remove any residual tetrahydrofuran. The percentage yield of losartan potassium is 90.04%.

While we have described our preferred embodiments in the examples here, variations on this disclosure can be discerned by one of skill in the art. Thus, we intend the legal coverage of our patent to be defined not by the specification and its examples, but by the appended claims.

We claim:

1. A process for manufacturing losartan potassium comprising:
   a. mixing approximately equimolar amounts of trityl losartan and a potassium tertiary alkoxide in a primary alcohol to create a reaction mixture;
   b. refluxing said reaction mixture to create a reaction mass comprising losartan potassium.

2. The process of claim 1, wherein said potassium tertiary alkoxide comprises potassium tertiary butoxide.

3. The process of claim 1, wherein said primary alcohol comprises methanol.

4. The process of claim 1, further comprising:
   c. removing from said reaction mass at least some of said primary alcohol;
   d. adding to said reaction mass a crystallization solvent; and
   e. crystallizing from said reaction mass losartan potassium.

5. The process of claim 4, wherein said crystallization solvent is selected from the group consisting of: isopropyl alcohol; tetrahydrofuran; and a combination of isopropyl alcohol and tetrahydrofuran.

6. The process of claim 5, wherein said crystallization solvent is tetrahydrofuran.

7. The process of claim 5, wherein said crystallization solvent is isopropyl alcohol.

* * * * *

UNITED STATES PATENT AND TRADEMARK OFFICE
CERTIFICATE OF CORRECTION

PATENT NO. : 6,916,935 B2
APPLICATION NO. : 10/431847
DATED : July 12, 2005
INVENTOR(S) : Ashok Kumar et al.

It is certified that error appears in the above-identified patent and that said Letters Patent is hereby corrected as shown below:

On Title page, Col. 1, at item (60) is hereby amended to add:

-- This application further claims priority from India National patent application Serial No. 335/MUM/2003, filed April 3, 2003 --

Signed and Sealed this

Eleventh Day of July, 2006

JON W. DUDAS
*Director of the United States Patent and Trademark Office*